(12) United States Patent
Nakamura

(10) Patent No.: US 7,375,880 B2
(45) Date of Patent: May 20, 2008

(54) MOUTH SWITCH MECHANISM FOR OPERATION MICROSCOPE

(75) Inventor: Katsushige Nakamura, Tokyo (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 0 days.

(21) Appl. No.: 11/578,573

(22) PCT Filed: Apr. 14, 2005

(86) PCT No.: PCT/JP2005/007209

§ 371 (c)(1),
(2), (4) Date: Oct. 16, 2006

(87) PCT Pub. No.: WO2005/099609

PCT Pub. Date: Oct. 27, 2005

(65) Prior Publication Data

US 2007/0206274 A1    Sep. 6, 2007

(30) Foreign Application Priority Data

Apr. 16, 2004   (JP) .............................. 2004-122001

(51) Int. Cl.
*G02B 21/00* (2006.01)
(52) U.S. Cl. ..................................... 359/384; 359/368
(58) Field of Classification Search ........ 359/368–390, 359/896
See application file for complete search history.

(56) References Cited

U.S. PATENT DOCUMENTS

| | | | |
|---|---|---|---|
| 3,887,267 A | 6/1975 | Heller | ........................ 359/389 |
| 4,912,388 A * | 3/1990 | Tanaka et al. | .............. 318/640 |
| 5,661,598 A * | 8/1997 | Tomioka | ..................... 359/388 |
| 2002/0148462 A1* | 10/2002 | Fugelsang et al. | ..... 128/200.14 |
| 2004/0090668 A1 | 5/2004 | Muller et al. | ............... 359/368 |

FOREIGN PATENT DOCUMENTS

| | | |
|---|---|---|
| JP | 08-107902 | 4/1996 |
| JP | 2001-243011 | 9/2001 |
| JP | 2003-344780 | 12/2003 |

* cited by examiner

*Primary Examiner*—Thong Nguyen
(74) *Attorney, Agent, or Firm*—Cheng Law Group PLLC

(57) ABSTRACT

A mouth switch is provided for a multifunction operation microscope (1). Signals to be outputted to the operation microscope can be switched from one provided when only a long main lever (21) is held with a mouth (lips, teeth, and the like) to another provided when a sub-lever (25) is held together with the main lever. Even if the number of functions to control increases, the mouth switch can cope with them. The mouth switch can change signals through the simple operation of holding the levers with a mouth, and therefore, possibility of an operation error can be reduced. As a changeover switch (22) is OFF, the mouth switch provides four kinds of signals including focus-up, focus-down, zoom-in, and zoom-out signals, and as for ON state, other four kinds of signals relating to X(+) direction, X(−) direction, Y(+) direction, and Y(−) direction for shifting field of view are provided.

16 Claims, 6 Drawing Sheets

MOUTH SWITCH MECHANISM FOR OPERATION MICROSCOPE

FIELD OF THE INVENTION

The present invention relates to a mouth switch for controlling an operation microscope.

BACKGROUND OF THE INVENTION

In the fields of brain surgery, cardiac surgery, and the like, an operation microscope is used to observe an affected part and conduct an operation in an enlarged field of view. The operation microscope used for such surgery has a plurality of functions such as focus adjustment and zoom adjustment. An operator keeps his or her eyes in contact with eyepieces of the operation microscope and uses both of his or her hands for the operation. Accordingly, the functions of the microscope are generally changed from one to another with a footswitch placed on the floor. The footswitch is provided with a plurality of control switches that are manipulated by the sole of a foot of the operator to change the functions from one to another.

BRIEF SUMMARY OF THE INVENTION

According to such a conventional technique, the footswitch must be used to select and control one of the functions of the operation microscope. As the number of functions of the operation microscope increases, the number of control switches arranged for the footswitch must be increased to increase the risk of causing erroneous operation. For this, a recently developed tool replacing the foot-manipulated footswitch is a mouth switch that is manipulated with a mouth. What is waited for is a mouth switch capable of achieving multiple functions. In view of the conventional technique, the present invention provides a mouth switch for an operation microscope, capable of controlling multiple functions.

According to a first technical aspect of the present invention, there is provided a mouth switch mechanism for an operation microscope, having a first mouth-operable lever attached to a body of a mouth switch so that the first lever can tilt and a second mouth-operable lever attached to the first mouth-operable lever so that the second lever can tilt. The second mouth-operable lever is in parallel with the first mouth-operable lever and a front end of the second mouth-operable lever is at an intermediate position of the first mouth-operable lever. When only the first mouth-operable lever is operated with a mouth, the mouth switch mechanism outputs a first signal to control the operation microscope. When the first mouth-operable lever and second mouth-operable lever are together operated with the mouth, the mouth switch mechanism outputs a second signal that is different from the first signal, to control the operation microscope.

According to a second technical aspect of the present invention, the mouth switch mechanism further has a tongue formed at a front end of the first mouth-operable lever and a protruding portion formed at an intermediate part between the front end and a base end of the first mouth-operable lever in the vicinity of the front end of the second mouth-operable lever.

According to a third technical aspect of the present invention, the mouth switch mechanism of the first technical aspect further has a first changeover switch positionally fixed to the mouth switch body and provided with a movable actuator to which the first mouth-operable lever is attached and a second changeover switch positionally fixed to the first mouth-operable lever and provided with a movable actuator to which the second mouth-operable lever is attached.

BRIEF DESCRIPTION OF THE DRAWINGS

FIG. 9 is a view showing four kinds of functions provided when the changeover switch is ON.

DETAILED DESCRIPTION OF THE INVENTION

An embodiment of the present invention will be explained with reference to FIGS. 1 to 9. An operation microscope 1 is in an operation room and is supported with a support mechanism 2 such as a stand unit. The support mechanism 2 has an X-Y driver 3 serving as an electric control mechanism that can move the operation microscope 1 as a whole in an imaginary plane defined by intersecting directions (X- and Y-axis directions). Namely, an optical axis Lob of an objective lens of the operation microscope 1 is translated in directions perpendicular to the optical axis to change a field of view so that a focal plane (focal depth range) of the objective lens comes in an affected part. According to the embodiment, a field of view is represented with a horizontal plane in which X and Y axes orthogonally crosses.

Figure 1:
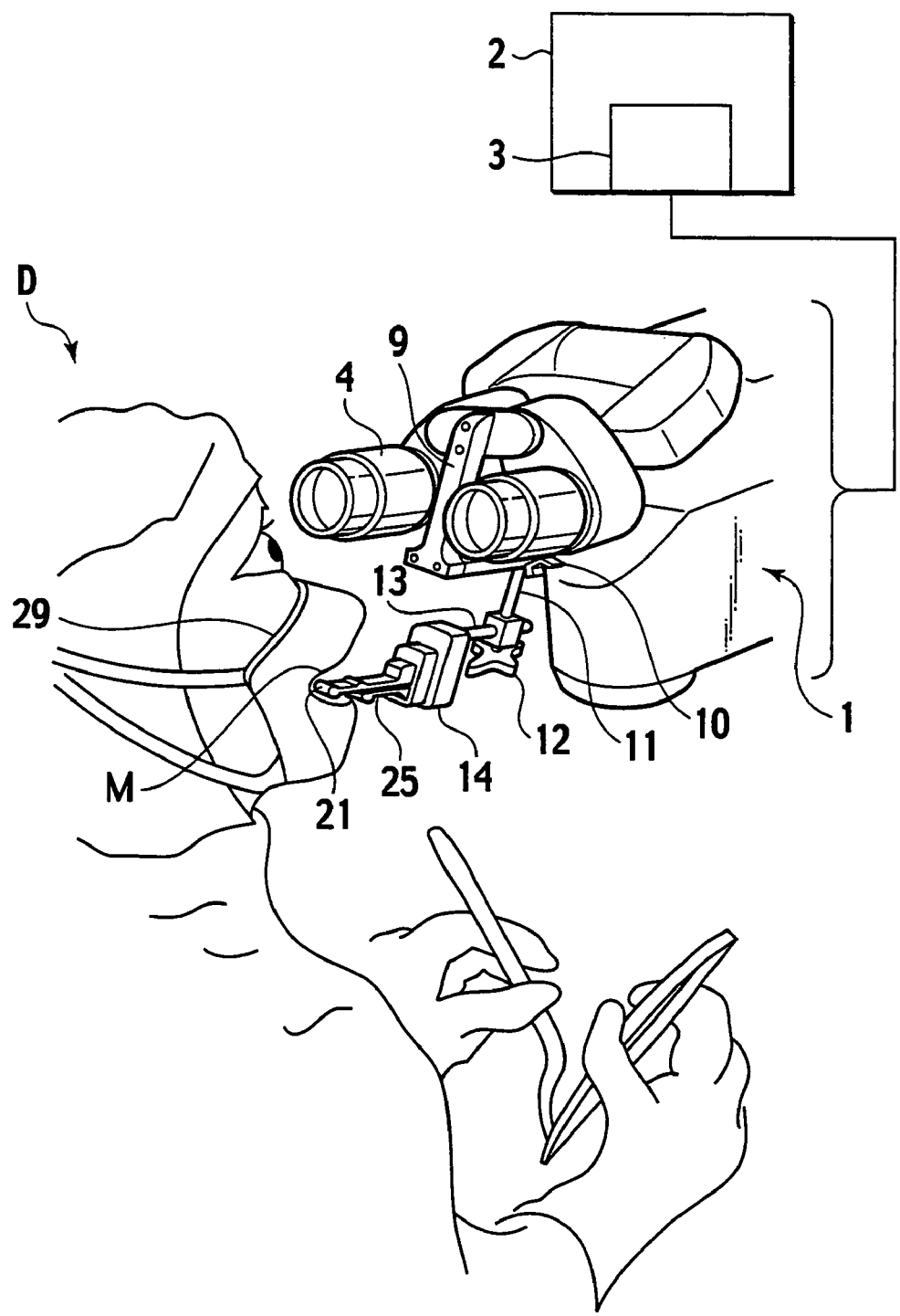
FIG. 1 is a perspective view showing a mouth switch for an operation microscope according to an embodiment of the present invention.
Figure 2:
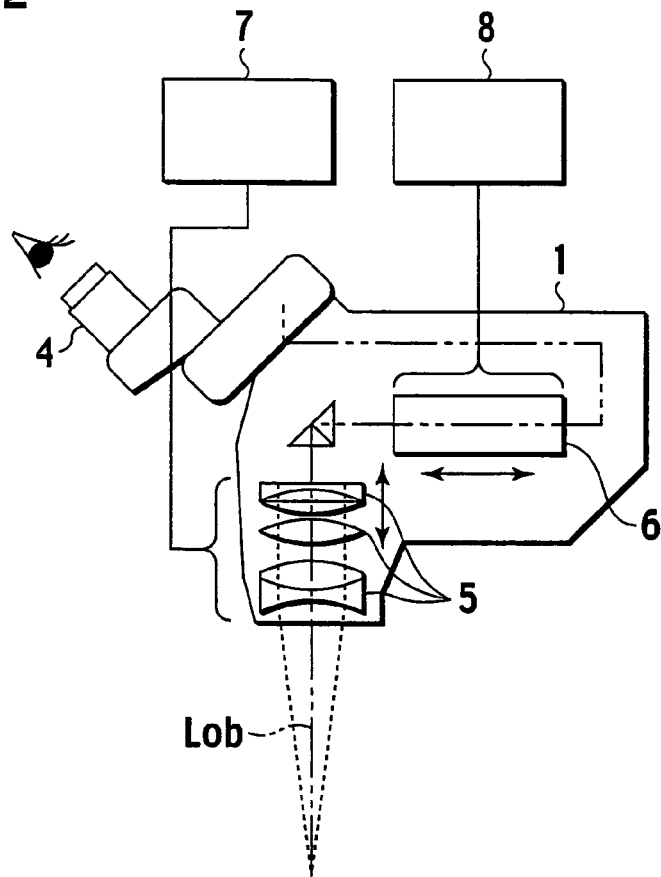
FIG. 2 is a schematic sectional view showing focus adjustment and zoom adjustment of the operation microscope.

The operation microscope 1 is a stereomicroscope having two eyepieces 4. As shown in FIG. 2, the operation microscope 1 includes a focusing lens 5 in a vertical direction and a zoom lens 6 in a horizontal direction. The focusing lens 5 is focused with a focus adjust mechanism 7 which is an electric control mechanism. The zoom lens 6 is zoom-adjusted with a zoom adjust mechanism 8 which is an electric control mechanism.

Figure 3:
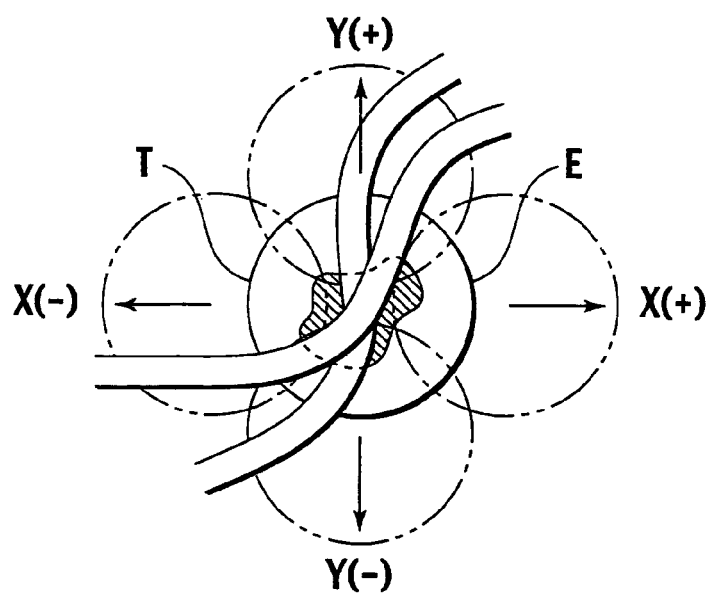
FIG. 3 is a schematic view showing movement and adjustment of a field of view.
Figure 4:
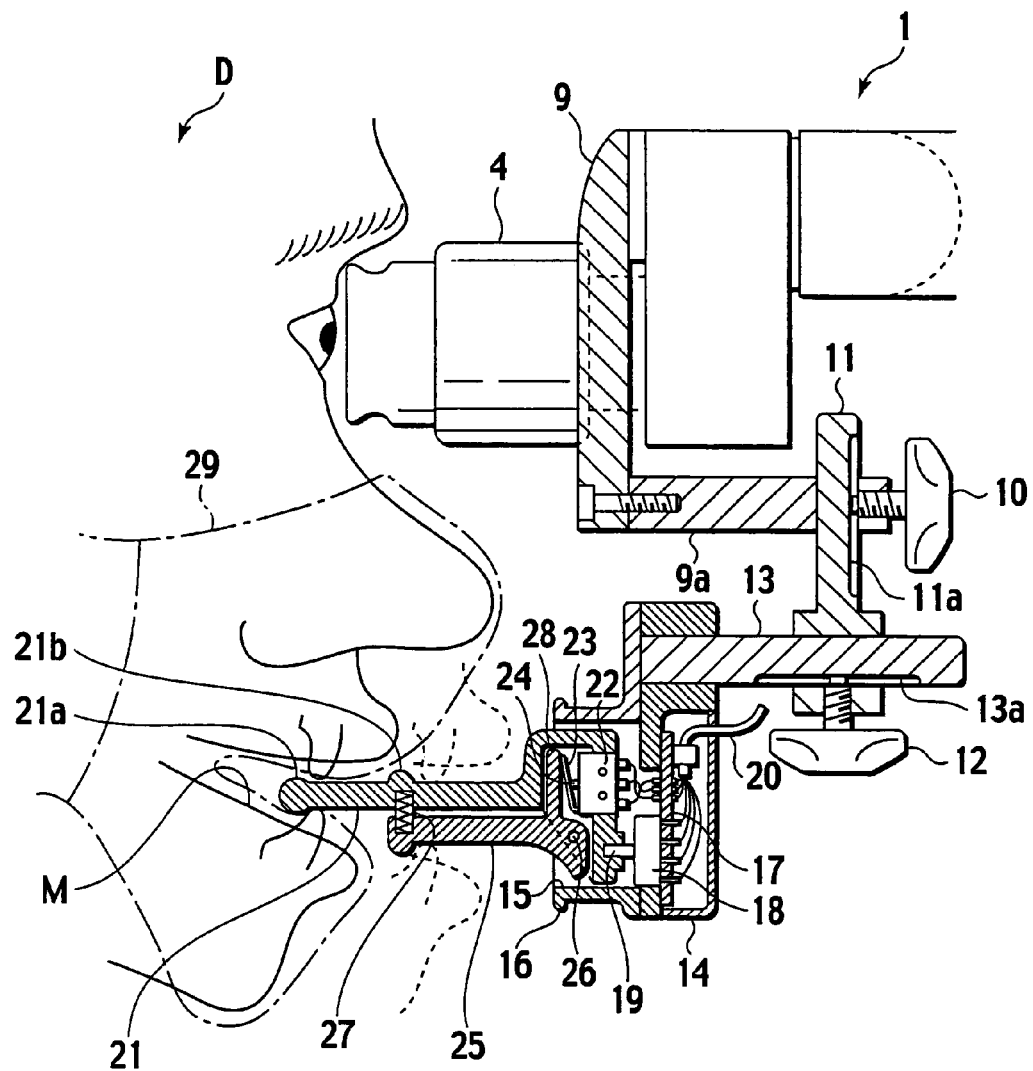
FIG. 4 is a sectional view showing the mouth switch.
Figure 5:
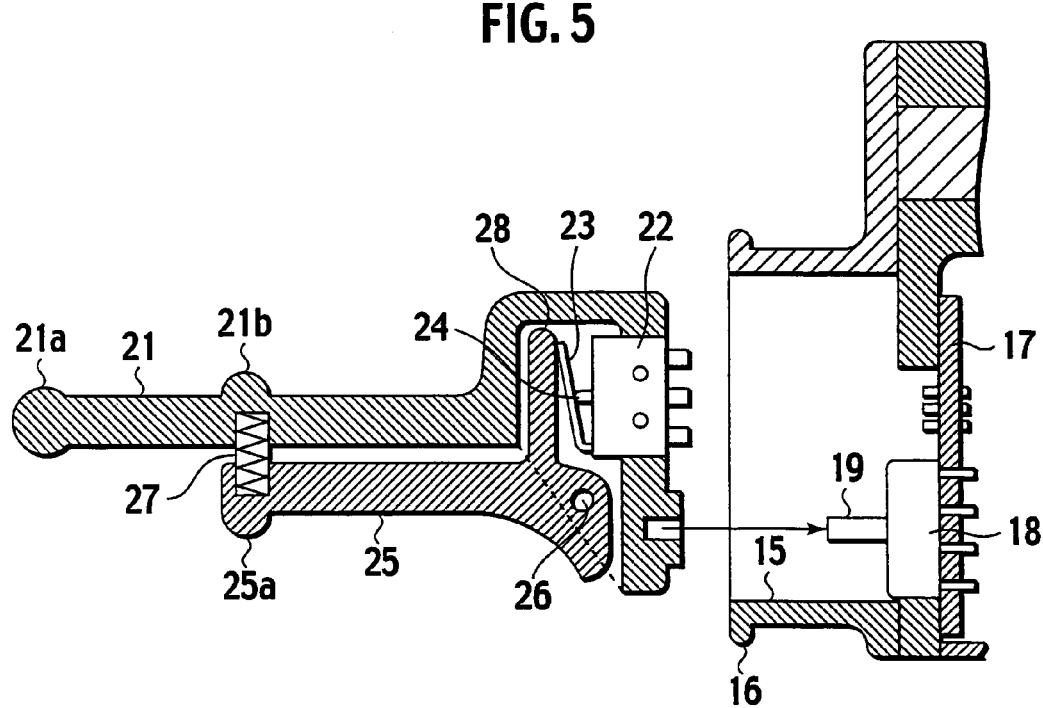
FIG. 5 is an exploded sectional view showing a fitting structure of a main lever to a joystick switch.
Figure 6:
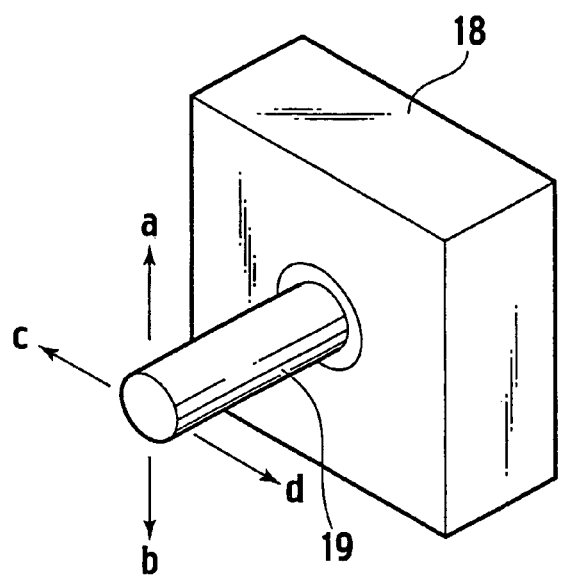
FIG. 6 is a perspective view showing the joystick switch.
Figure 7:
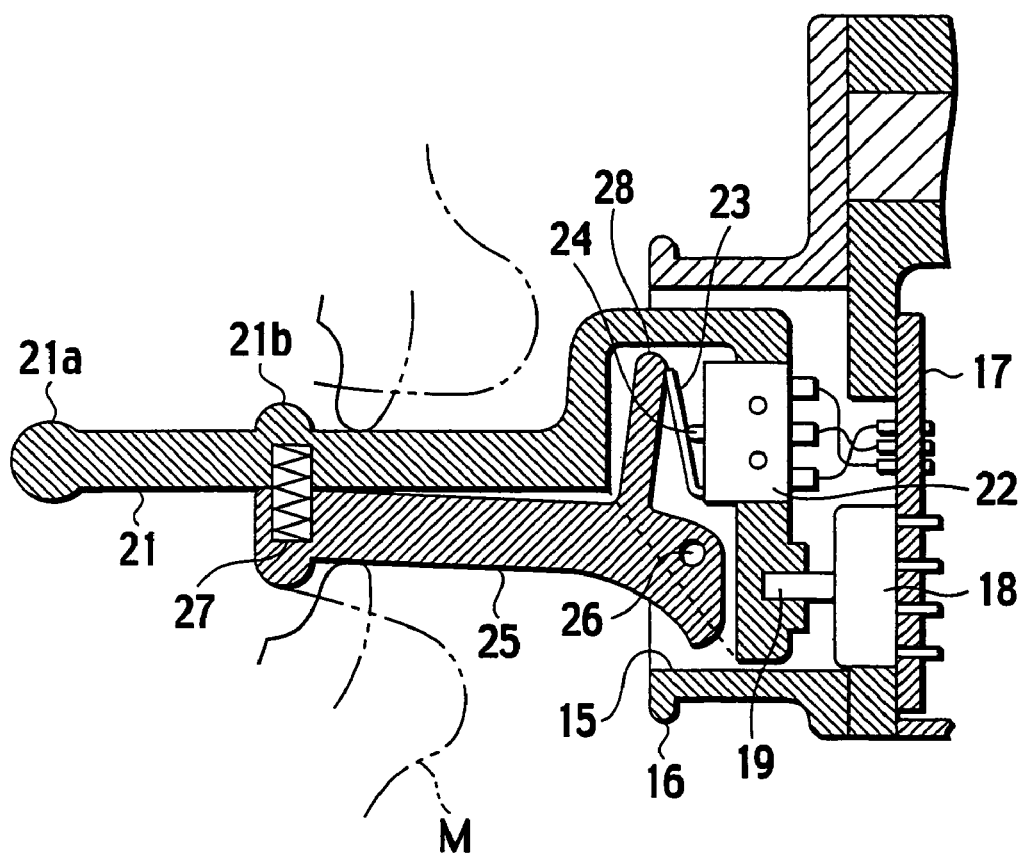
FIG. 7 is a sectional view showing a sub-lever pressed with the mouth.

As shown in FIG. 3, the X-Y driver 3 horizontally moves the operation microscope 1 as a whole, to move an observation field of view E relative to the affected part T as a target. Namely, the operation microscope (objective lens) can be moved so that the focal plane of the objective lens may cross the field of view E containing the affected part T. The range of movement of the operation microscope 1 is very small, and therefore, the field of view E can be also moved by turning the operation microscope 1.

An operator D brings his or her eyes in contact with the eyepieces 4 between which an L-shaped support lever 9 is arranged. The support lever 9 has a horizontal lower part 9a provided with a vertical bar 11 that is vertically adjustable with a clamp 10. The vertical bar 11 has a groove 11a formed in a longitudinal direction. A front end of the clamp 10 can be stopped in the groove 11a, to prevent the vertical bar 11 from rotating or vertical moving. The vertical bar 11 has a lower part 11a provided with a horizontal bar 13 that is horizontally adjustable with a clamp 12. The horizontal bar 13 has a groove 13a formed in a longitudinal direction. By stopping a front end of the clamp 12 in the groove 13a, the horizontal bar 13 can be prevented from rotating or horizontally moving.

A front end of the horizontal bar 13 is fixed to a case 14. Namely, bodies 14 and 18 of a mouth switch are positionally fixed to the operation microscope 1 and eyepieces 4 with the support lever 9, the vertical bar 11, and the horizontal bar 13. The case 14 has an opening 15 being oriented to the front side and having a square cylinder shape. The opening 15 is surrounded with a flange 16 for fitting a sterile drape (not shown). A board 17 is fixed inside the case 14. A joystick switch 18 is fixed to the board 17 in such a way that a stick 19 of the joystick switch serving as a movable actuator is oriented to the opening 15. The stick 19 is tiltable in four directions (a, b, c, and d in FIG. 6) so that the joystick switch 18 may output four kinds of signals. The joystick switch 18 has wiring 20 connected to the focus adjust mechanism 7, zoom adjust mechanism 8, and X-Y driver 3.

A proximal portion of a long main lever 21 is fixed to the joystick switch 18. The main lever 21 is fixed only to the stick 19 that supports the main lever as a whole. The main lever 21 has at its distal portion a first operation part 21a and a second operation part 21b at an intermediate position of a base between the distal portion and the proximal portion thereof. The first operation part 21a and second operation part 21b each has a protruding portion, so that the operator D can recognize their positions when the operator D holds them with the mouth M. The first operation part 21a has an enlarged diameter at the front end of the main lever 21 to form a sphere or tongue.

The first operation part 21a and second operation part 21b may be held with the mouth M, or the vicinities thereof may be held with the mouth M. Holding them with the mouth M typically means to lightly hold them with the lips or teeth. It is also possible to manipulate them with the tongue.

The main lever 21 has a hollow base in which a changeover switch 22 is fixed. The changeover switch 22 turns on when a button 24 is pushed with a detection lever 23.

A sub-lever 25 is arranged under the main lever 21. At the base of the main lever 21, a proximal portion of the sub-lever 25 is supported to turn around a shaft 26. The main lever 21 and sub-lever 25 are juxtaposed to each other in such that the longitudinal axes are oriented substantially to the same direction. The sub-lever 25 is shorter than the main lever 21. The distal portion 25a of the sub-lever 25 positionally corresponds to the second operation part 21b of the main lever 21. Between the sub-lever 25 and the main lever 21, a biasing element 27 such as a spring or a magnet is arranged to bias the levers and secure a predetermined gap.

The proximal portion of the sub-lever 25 has an upward projection 28. When the sub-lever 25 is tilted toward the main lever 21, the projection 28 acts on the movable actuator of the changeover switch 22. Namely, the projection 28 pushes the button 24 of the changeover switch 22 through the detection lever 23. When the button 24 of the changeover switch 22 is pushed, the four kinds of signals outputted from the joystick switch 18 are alternatively changed with another set of four signals.

Figure 8:
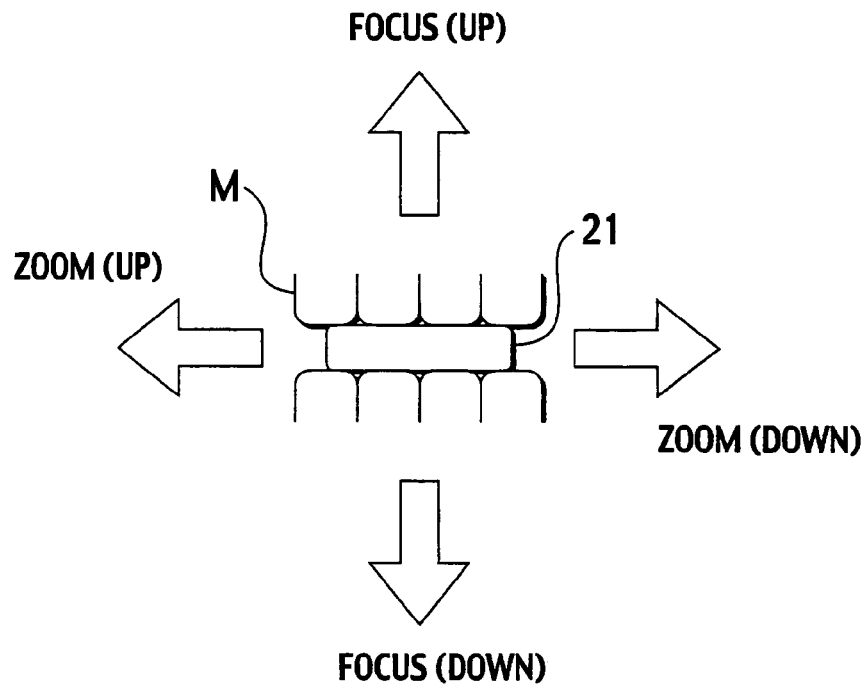
FIG. 8 is a view showing four kinds of functions provided when a changeover switch is OFF.
Figure 9:
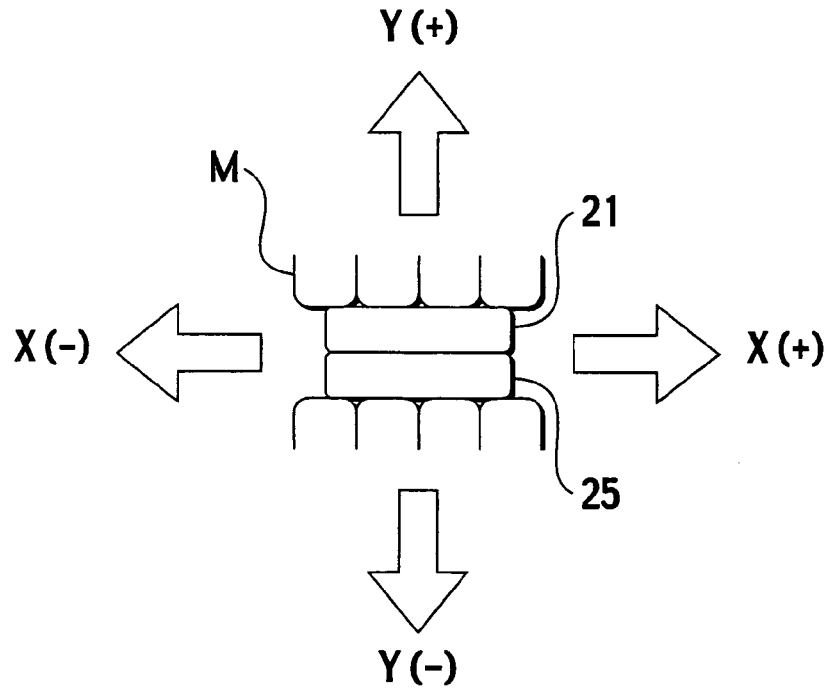

More precisely, the four signals (first signals) provided as the changeover switch 22 is OFF (first state) are focus-up and focus-down signals corresponding to up and down directions and zoom-in and zoom-out signals corresponding to left and right directions, as shown in FIG. 8. The four signals (second signals) provided when the changeover switch 22 is ON (second state) are signals to shift a field of view in operation directions of the main lever 21, i.e., a Y-axis positive direction (Y+), a Y-axis negative direction (Y−), an X-axis positive direction (X+), and an X-axis negative direction (X−) along the X and Y axes that intersect each other.

According to the mouth switch of this embodiment, the operator D manipulates the two clamps 10 and 12 at the start of an operation and adjusts the main lever 21 just to the mouth M with the operator's eyes being in contact with the eyepieces 4 of the operation microscope 1. After starting the operation, both the hands of the operator D are busy for the operation. Even so, the first operation part 21a of the main lever 21 can be held with the mouth M and can be shifted in up, down, left, and right directions to conduct focus adjustment and zoom adjustment in a field of view. The mouth M can hold the main lever 21 together with a mask 29. Even so, the mask 29 will not interfere with the sub-lever 25.

To shift observation field of view E, the second operation part 21b of the main lever 21, which is behind the first operation part 21a, and the distal portion of the sub-lever 25 are held with the mouth M. The mouth M holds the structure in a vertical direction to cancel the holding force, and therefore, no shake/fluctuation occurs in the field of view of the operation microscope 1. When held with the mouth M, the sub-lever 25 turns around the shaft 26, to turn on the changeover switch 22. Then, the main lever 21 can provide a field of view moving signal to move the field of view to a required direction. If the main lever 21 and sub-lever 25 are moved diagonally, the field of view E will shift in a composite direction.

Once the field of view E has moved to the required position, the holding position of the mouth M is returned to the first operation part 21a, to conduct focus adjustment and zoom adjustment for continuing the operation.

EFFECT OF INVENTION

According to the present invention, the long main lever and short sub-lever are employed so that sets of signals supplied to the operation microscope are adjustable according to the situations when only the main lever is held with the mouth or the main lever and sub-lever are held with the mouth. Furthermore, even if the number of control functions increases, the present invention can cope with such increases. The present invention can change signal sets through the simple operation of holding the levers with a mouth, and therefore, operational errors can be remarkably reduced.

The present invention supports the main lever by fixing it to the stick of the joystick switch. The main lever supports the sub-lever for operating the changeover switch. This simple structure can support the main lever and operate the changeover switch.

According to the present invention, a function group concerning focusing and zooming and a function group concerning a field of view movement can be switched from one to another with the changeover switch. This improves the operability of the operation microscope.

INDUSTRIAL APPLICABILITY

In the above-mentioned embodiment, the turnable sub-lever 25 is attached to the main lever 21. If a configuration of operating the changeover switch 22 by holding the same with the mouth M is employed, the sub-lever may be of a push type or any other type. The "ON" state of the changeover switch 22 does not strictly mean an electrically conductive state. It may be an execution state of an original switching function of the changeover switch 22. For example, the changeover switch 22 may be always conductive, and when de-energized/shut-off, may establish the "ON" state. The joystick switch 18 may have any structure to output four kinds of signals. These signals may partly be disabled, to output, for example, only two kinds of signals.

The invention claimed is:

1. A mouth switch mechanism for an operation microscope, comprising:
   a first mouth-operable lever attached to and tiltable with respect to a body of a mouth switch; and
   a second mouth-operable lever attached to and tiltable with respect to the first mouth-operable lever, the second mouth-operable lever being in parallel with the first mouth-operable lever and a distal portion of the second mouth-operable lever being positioned at an intermediate position of the first mouth-operable lever, wherein
   as only the first mouth-operable lever is operated with a mouth, the mouth switch mechanism outputs a first signal to control the operation microscope; and
   as the first mouth-operable lever and second mouth-operable lever are together operated with the mouth, the mouth switch mechanism outputs a second signal different from the first signal to control the operation microscope.

2. The mouth switch mechanism for an operation microscope according to claim 1, wherein
   the mouth switch mechanism further comprises a first protruding portion formed at a distal portion of the first mouth-operable lever and a second protruding portion formed at an intermediate part between the distal portion and a proximal portion of the first mouth-operable lever in the vicinity of the distal portion of the second mouth-operable lever.

3. The mouth switch mechanism for an operation microscope according to claim 2, further comprising:
   a first changeover switch positionally fixed to the mouth switch body and provided with a movable actuator to which the first mouth-operable lever is attached; and
   a second changeover switch positionally fixed to the first mouth-operable lever and provided with a movable actuator to which the second mouth-operable lever is attached.

4. The mouth switch mechanism for an operation microscope according to claim 3, wherein:
   the first changeover switch outputs a signal selected from a plurality of signals according to an operation of the first mouth-operable lever; and
   the second changeover switch outputs a signal selected from a plurality of signals according to an operation of the second mouth-operable lever.

5. The mouth switch mechanism for an operation microscope according to claim 4, wherein:
   the signal outputted from the second changeover switch has a first state or a second state;
   as the signal outputted from the second changeover switch is in the first state, a signal outputted from the first changeover switch is the first signal and is related to any one of focus-up, focus-down, zoom-in, and zoom-out actions; and
   as the signal outputted from the second changeover switch is in the second state, the signal outputted from the first changeover switch is the second signal and is related to any one of a first shifting direction of field of view, a direction opposite to the first shifting direction, a second shifting direction of field of view intersecting the first shifting direction, and a direction opposite to the second shifting direction.

6. The mouth switch mechanism for an operation microscope according to claim 4, wherein the first changeover switch is a joystick switch.

7. The mouth switch mechanism for an operation microscope according to claim 5, wherein the first changeover switch is a joystick switch.

8. The mouth switch mechanism for an operation microscope according to claim 2, wherein the mouth switch body is positionally fixed to the operation microscope.

9. The mouth switch mechanism for an operation microscope according to claim 1, further comprising:
   a first changeover switch positionally fixed to the mouth switch body and provided with a movable actuator to which the first mouth-operable lever is attached; and
   a second changeover switch positionally fixed to the first mouth-operable lever and provided with a movable actuator to which the second mouth-operable lever is attached.

10. The mouth switch mechanism for an operation microscope according to claim 9, wherein:
    the first changeover switch outputs a signal selected from a plurality of signals according to an operation of the first mouth-operable lever; and
    the second changeover switch outputs a signal selected from a plurality of signals according to an operation of the second mouth-operable lever.

11. The mouth switch mechanism for an operation microscope according to claim 10, wherein:
    the signal outputted from the second changeover switch has a first state or a second state;
    as the signal outputted from the second changeover switch is in the first state, a signal outputted from the first changeover switch is the first signal and is related to any one of focus-up, focus-down, zoom-in, and zoom-out actions; and
    as the signal outputted from the second changeover switch is in the second state, the signal outputted from the first changeover switch is the second signal and is related to any one of a first shifting direction of field of view, a direction opposite to the first shifting direction, a second shifting direction of field of view intersecting the first shifting direction, and a direction opposite to the second shifting direction.

12. The mouth switch mechanism for an operation microscope according to claim 11, wherein the first changeover switch is a joystick switch.

13. The mouth switch mechanism for an operation microscope according to claim 10, wherein the first changeover switch is a joystick switch.

14. The mouth switch mechanism for an operation microscope according to claim 1, wherein the mouth switch body is positionally fixed to the operation microscope.

15. The mouth switch mechanism for an operation microscope according to claim 1, wherein
    the mouth switch mechanism further comprises a tongue or a sphere formed at a front end of the first mouth-operable lever.

16. The mouth switch mechanism for an operation microscope according to claim 1, wherein
    the mouth switch mechanism further comprises a third protruding portion formed at the distal portion of the second mouth-operable lever.

* * * * *